United States Patent [19]
Palmiter et al.

[11] Patent Number: 5,583,009
[45] Date of Patent: Dec. 10, 1996

[54] METHOD OF PREPARING RECOMBINANT PROTEINS IN TRANSGENIC ANIMALS CONTAINING METALLOTHIONEIN GENE ELEMENTS THAT BESTOW TISSUE-INDEPENDENT COPY NUMBER-DEPENDENT, POSITION-INDEPEDENT GENE EXPRESSION

[75] Inventors: Richard Palmiter, Seattle, Wash.; Eric P. Sandgren, Philadelphia; Ralph L. Brinster, Gladwyne, both of Pa.

[73] Assignees: University of Washington, Seattle, Wash.; The Trustees of the University of Pennsylvania, Philadelphia, Pa.

[21] Appl. No.: 986,963

[22] Filed: Dec. 8, 1992

[51] Int. Cl.$^6$ .............................. C12P 21/02; C12P 21/00; C12N 15/09; C07H 21/04
[52] U.S. Cl. ...................... 435/691; 435/71.1; 435/172.1; 435/172.3; 536/23.1; 536/24.1; 800/2; 935/34; 935/53; 935/70
[58] Field of Search ................................ 435/172.3, 69.1, 435/71.1; 800/2; 514/44; 536/23.1, 24.1, 23.5

[56] References Cited

PUBLICATIONS

Clark et al. 1987 Tibtech 5:20–24.
Shuman 1991 Experientia 47:897–905.
Ledley 1991 Human Gene Therapy 2:77–83.
Karson et al. 1992 Journal of Reproductive Medicine 37(6):508–514.
Brinster et al. 1981. Cell 27:223–231.
Palmiter et al. 1986. Ann Rev Genet. 20:465–499.
Science, vol. 244, Jun. 16, 1989, Theodore Friedmann, "Progress Toward Human Gene Therapy", pp. 1275–1281.
Science, vol. 226, Oct. 26, 1984, W. French Anderson, "Prospects for Human Gene Therapy", pp. 401–409.
Cell, vol. 51, pp. 975–985, Dec. 24, 1987, Frank Grosveld, et al., "Position–Independent, High–Level Expression of the Human Beta–Globin Gene in Transgenic Mice".
Proceedings of the National Academy of Science, USA, vol. 82, pp. 6384–6388, Oct. 1985, Dorothy TUAN, et al., "The 'Beta–Like–Globin'Gene Domain in Human Erythroid Cells".
Proceedings of the National Academy of Science, USA, vol. 83, pp. 1359–1363, Mar. 1986, William C. Forrester, et al., "A Developmentally Stable Chromatin Structure in the Human Beta–Globin Gene Cluster".
Molecular and Cellular Biology, Sep. 1993, pp. 5266–5275, vol. 13, No. 9, Richard D. Palmiter, et al., "Distal Regulatory Elements From the Mouse Metallothionein Locus Stimulate Gene Expression in Transgenic Mice".
Theriogenology, vol. 37, No. 1, Jan. 1992, R. J. Wall, et al., "Matrix Attachment Sequences Improve Genetic Control of a Mammory Gland Transgene in Mice", p. 319.
Proceedings of the National Academy of Science, USA, vol. 89, Aug. 1992, pp. 6943–6947, Robert A. McKnight, et al., "Matrix–Attachment Regions Can Impart Position–Independent Regulation of a Tissue–Specific Gene in Transgenic Mice".
Nucleic Acids Research, vol. 19, No. 7, 1991, Sara Pruzina, et al., "Hypersensitive Site 4 of The Human Beta–Globin Locus Control Region", pp. 1413–1419.
Nature, vol. 355, Jan. 16, 1992, Gary Felsenfeld, "Chromatin as an Essential Part of the Transcriptional Mechanism", pp. 219–224.

(List continued on next page.)

*Primary Examiner*—Brian R. Stanton
*Attorney, Agent, or Firm*—Oblon, Spivak, McClelland, Maier & Neustadt, P.C.

[57] ABSTRACT

Vertebrate gene locus control regions linked to a structural gene of interest and inserted into a transgenic animal are capable of bestowing tissue-independent, copy number-dependent, position-independent gene expression. Recombinant proteins of interest encoded by structural genes linked to the metallothionein locus control regions may be prepared following expression in transgenic animal hosts.

6 Claims, 7 Drawing Sheets

OTHER PUBLICATIONS

The EMBO Journal, 1990, vol. 9, No. 7, pp. 2159–2167, Sjaak Philipsen, et al., "The Beta–Globin Dominant Control Region: Hypersensitive Site 2".

Annual Review of Biochemistry, vol. 55, 1986, D. H. Hamer, "Metallothionein", pp. 913–951.

Trends in Genetics, vol. 6, No. 7, Jul. 1990, T. M. Townes, et al., "Human Globin Locus Activation Region (LAR): Role in Temporal Control", pp. 219–223.

Journal of Cellular Biochemistry, vol. 52, pp. 23–36, 1993, Teni Boulikas, "Homeodomain Protein Binding Sites, Inverted Repeats, and Nuclear Matrix Attachment Regions Along the Human Beta–Globin Gene Complex".

Journal of Cellular Biochemistry, vol. 52, 1993, pp. 14–22, Teni Boulikas, "Nature of DNA Sequences at the Attachment Regions of Genes to the Nuclear Matrix".

The EMBO Journal, vol. 9, No. 9, pp. 2843–2848, 1990, Constanze Bonifer, et al., "Tissue Specific and Position Independent Expression of the Complete Gene Domain for Chicken Lysozyme in Transgenic Mice".

An 17256, 1993, I. L. Goldman, et al., "Investigating the Expression of the Gene Responsible for the Cattle Growth Hormone in a Rabbit Being Transgenic in Respect of the mMT 1/bGHatt Gene Construction Comprising the Matrix Attachment Region Element".

An 20823z, 1993, I. L. Goldman, et al., "Expression of the gene Responsible for the Cattle Growth Hormone in a Rabbit Being Transgenic With Respect to the mMT 1/bGHatt Gene construction Comprising the Matrix Attachment Region Element".

METHOD OF PREPARING RECOMBINANT PROTEINS IN TRANSGENIC ANIMALS CONTAINING METALLOTHIONEIN GENE ELEMENTS THAT BESTOW TISSUE-INDEPENDENT COPY NUMBER-DEPENDENT, POSITION-INDEPEDENT GENE EXPRESSION

The present invention is based on work in part funded by the National Institute of Health (HD 09172 and HD 23657).

BACKGROUND OF THE INVENTION

1. Field of the Invention

The present invention relates to gene expression, including regulation, in mammalian cell and transgenic animal systems.

2. Discussion of the Background

Although many characterized structural genes, together with control sequences, have been inserted into vectors and used to transform host cells, there remains a need for expression vectors capable of exhibiting high levels of expression in varied systems, and which preferably can be regulated. In particular, expression vectors for use in either mammalian cell lines or transgenic systems, possessing these characteristics are becoming increasingly important, both for the commercial production of desired polypeptides and for the development of therapies and/or treatments for diseases and genetic disorders.

The level of gene expression obtainable in transgenic animals, to date, has often been very low and sometimes undetectable. The reasons for this low expression are poorly understood, but may relate to inefficient activation of gene expression during development. In general, intact genes with sufficient flanking sequences are expressed best, chimeric genes made of heterologous promoters and intact structural genes are expressed quite reliably, whereas cDNA construct with heterologous promoters are the most troublesome.

Some of the inventors have been trying to find a general method for expressing cDNA constructs in transgenic mice (*Brinster et al, Proc. Nat. Acad. Sci. USA* (1988) 85: 836–840; *Palmiter et al, Proc. Nat. Acad. Sci. USA* (1991) 88:478–482. Because cDNA lacks introns, the inventors initially thought that adding introns to these constructs might improve expression, and it does in some situations (*Palmiter et al*, 1991). Although one generally thinks of introns as having a major role in RNA splicing, the inventors believe that introns affect gene expression at the transcriptional level, perhaps by allowing favorable phasing of nucleosomes relative to important cis-acting promoter elements.

When making transgenic animals, e.g. transgenic mice, by the microinjection method, the transgenes are thought to integrate randomly into the genome and they usually integrate in tandem, head-to-tail arrays. Although the genes may be expressed from many random integration sites, the level of expression in, for example, different mouse lines varies tremendously and is usually unrelated to transgene copy number. The general explanation to this phenomena is that the transgenes are subject to local chromosomal effects, called "position effects".

It is thought that genes may normally reside in chromosomal domains that insulate them from neighboring chromosomal effects. Experimental support for this latter suggestion comes from the work on the globin locus in which sequences flanking the locus, now called locus control regions (LCR), can convey position-independency and copy number-dependency to globin genes (*Grosveld et al, Cell* (1987) 51:975–985) and to heterologous genes. However, the LCR from the globin gene only functions in erythroid cells and its use is thus very limited. Being interested in a general solution to the gene expression problem, the inventors have sought sequences that have a similar property but are capable of functioning in many, if not all, cell types.

Metallothionein (MT) genes encode small proteins that bind heavy metals such as zinc, cadmium and copper by virtue of their high cysteine content. These genes have been found in all eukaryotic organisms examined and they are thought to play an important role in metal homeostasis and resistance to metal toxicity (for a review see: *Kagi et al, Experientiia Supplementum* (1987), 52, Birkhauser Verlag, Basel). In most mammals there are at least two similar MT genes, MT-I and MT-II, that as far as is known serve identical functions. In the mouse, these genes are closely linked on chromosome 8 and they are coordinately regulated by metals, glucocorticoids and acute-phase stimulators (*Searle et al, Mol. Cell. Biol.* (1984) 4:1221–1230).

Many of the cis-acting elements that mediate the transcriptional responses to these stimuli have been located to within a few hundred base pairs upstream of the transcription start site (for review see: *Hamer, Annu. Rev. Biochem.* (1986) 55:913–951). MT genes are expressed in various cell types throughout mouse development and in most cells of the adult; their regulation in vivo is a complex function of cellular exposure to stimuli and the presence of appropriate signal transduction pathways (*Searle et al, Mol. Cell. Biol.* (1984) 4: 1221–1230; *De et al, J. Biol. Chem.* (1990) 265: 15267–15274).

The metallothionein (MT) promoter has been used to direct expression of a wide variety of reporter genes in transgenic mice (*Palmiter et al, Ann. Rev. Gen.* (1986) 20: 465–499). In general, one observes expression of the reporter gene in those tissues that normally express MT well, such as liver, kidney and intestine, and the expression is often inducible by heavy metals. However, the expression pattern of the reporter gene and its responsiveness to various stimuli rarely mimics that of the endogenous MT genes exactly and there are often bizarre exceptions such as expression in one tissue only. In addition, the level of expression is usually unrelated to transgene copy number (*Palmiter et al*, 1986).

These results suggest that while certain control elements may be functional, the expression of MT transgenes is strongly influenced by the site of chromosomal integration. All of these experiments are complicated by the fact that the reporter gene being used in conjunction with the MT promoter may markedly influence the expression pattern by affecting transcription and/or mRNA stability, and these effects may not parallel those of endogenous MT genes in all tissues.

Similar results have been observed when the DNA sequences which regulate the human β-globin gene were introduced 5' and 3' to various cloned globin genes (*Charnay et al, Cell* (1984) 38: 251–263; Wright et al, *Nature* (1983) 305: 333–336). When a β-globin gene containing these DNA sequences were introduced into mice, the gene was not expressed at the same level as the mouse β-globin gene and exhibited integration site dependent effects (*Townes et al, EMBO J.* (1985) 7: 1715. This was characterized by a highly variable expression of the transgene that did not correlate with the copy number of the injected gene in the mouse genome.

As noted above, Grosveld et al have demonstrated that when the human β-globin gene with its own promoter and enhancers ligated to DNA sequences that lie upstream of ε-globin gene and shown to be hypersensitive to DNase digestion, the expression pattern obtained in transgenic mice is position-independent and directly correlates to the number of inserted copies. However, the effect of these flanking regions is cell-specific and thus of limited use. The expression level per gene copy is at a similar level to that of endogenous globin genes in erythroid cells. In non-erythroid cells, low levels of expression are obtained, similar to those obtained when the flanking regions are not present (Blom van Assendelft et al, Cell (1989) 56: 969–977).

In a chromosome, the genetic material is packaged into a DNA/protein complex called chromatin which has the effect of limiting the availability of DNA for functional purposes. It has been established that many gene systems possess so-called DNA hypersensitive sites. Such sites representative putative regulatory regions, where the normal chromatin structure is altered by binding of proteins to specific DNA sequences. For example, DNaseI hypersensitive sites are often associated with the promoter and enhancer regions of active genes. The presence of DNaseI hypersensitive sites (in the vicinity of genes) that are not directly related to gene expression, suggests that they may mark the location of other important chromosomal functions, perhaps boundaries of chromosomal domains, origins of replication, or sites of attachment to nuclear matrix.

MacArthur et al (J. Biol. Chem. (1987) 7: 3466–3472) mapped DNaseI hypersensitive sites in a thymoma-derived cell line, S49. These cells are unusual in that neither of the MT genes are expressed nor inducible by metals. However, cadmium-resistant variants can be selected that express either MT-I, MT-II or both genes. DNaseI hypersensitive sites flanking the MT genes (about 6 kb 5' of the MT-II gene and 4 kb 3' of the MT-I gene) are present regardless of whether the MT genes are expressed, but new hypersensitive sites appear in the promoter regions of whichever MT genes are expressed after selection (MacArthur et al, 1987).

Several other genetic loci are also flanked by DNaseI hypersensitive sites, including the human β-globin locus (Tuan et al, Proc. Nat. Acad. Sci. U.S.A., (1985) 82: 6384–6388; Proc. Nat. Acad. Sci. U.S.A. (1986) 83: 1359–1363) and the chicken lysozyme gene (Sippel et al, Nucleic Acids and Molecular Biology 3, Springer Verlag: Berlin, 1988, pp. 1323–147).

Pruzina et al (Nucleic Acid Research (1991) 19: 1413–1419) defines an LCR of the human β-globin gene domain located upstream of the human β-globin multigene cluster and divided into four DNaseI hypersensitive sites (HS). The LCR HSS4 has been precisely mapped to a 280 bp fragment that has functional LCR activity in MEL cells and transgenic mice. The sequence of the 280 bp fragment is disclosed in this publication.

Philipsen et al (EMBO J. (1990) 9: 2159–2167) describes the hypersensitive site 2 (HS2) of the LCR of the human β-globin gene. The publication discloses a 225 bp fragment sufficient to direct high levels of expression of the human β-globin gene in a copy number dependent and integration site independent fashion. The sequence of the 225 bp fragment is also disclosed.

Talbot et al (Nature (1989) 338: 352–355) defines the human β-globin LCR region properties as described above. It is located in a 6.25 kb section of DNA found 5' of the human β-globin locus. This region allows high levels of expression of the human β-globin gene as well as a heterologous thymidine kinase gene in erythroid cells of transgenic mice.

Bonifer et al (EMBO J. (1990) 9: 2843–2848), discloses transgenic mice that carry the entire wild type chicken lysozyme gene domain including the 11.5 kilobase 5' flanking and 5.53 sequences (LCR or A-elements). The publication reports the cross species gene transfer ability of chicken genes in mammals resulting in high level macrophage-specific gene expression in the recipient mouse, and that the entire gene locus transferred into the mouse acts as an independent regulatory unit not requiring a specific chromosome position.

Steif et al (Nature, (1989) 341: 343–345) describes how a reporter gene encoding CAT flanked by 5' A-elements (LCRs) from the chicken lysozyme gene may have significant elevated expression in stably transfected cells and that the expression is independent of the chromosome position.

Reitman et al (Nature (1990) 348: 749–752) reports studies of chicken β-globin gene expression in transgenic mice. Chicken DNA elements that reportedly allow position independent expression that can function in mice are described. These elements are within 2 kb from the chicken globin gene demonstrating an intracluster location that differs from the LCR location found in human β-globin and chicken lysozyme.

Greaves et al (Cell (1989) 56: 979–986) describes LCR sequences located downstream from the human CD2 gene that activates high level T-cell specific expression in transgenic mice regardless of the site of the chromosome integration of the transgene.

The following publications are also of interest: Albitar et al, Mol. Cell. Bio. (1991) 11: 3786–3794; Constantoulakis et al, Blood (1991) 77: 1326–1333; Kulocik et al, J. Clin Invest. (1991) 87: 2142–2146; Talbot et al, EMBO J. (1991) 10: 1391–1398; Dillon et al, Nature (1991) 350: 352–354; Hanscombe et al, Genes and Devel. (1991) 5: 1387–1394; Catarina et al, Proc. Natl. Acad. Sci. (U.S.A.) (1990) 88: 1626–1630; Lavelle et al, Proc. Natl. Acad. Sci. U.S.A. (1990) 88: 7318–7322; Raich et al, Science (1990) 250: 1147–1149; Greaves et al, Nature (1990) 343: 183–185; Orkin, Cell (1990) 63: 665–672; Grosveld, Ann. New York Acad. of Sci. (1990) 6112: 152–159; Palmiter et al, Ann. Rev. Genet. (1986) 20: 465–499; Townes et al, EMBO J. (1985) 4: 1715–1723; Muller et al, Bone Marrow Transplantation (1990) 5: 13–14; Peters et al, Eur. J. Biochem. (1989) 182: 507–516; Fritton et al, Biol. Chem. Hoppe-Seyler (1987) 368: 111–119; and Theisen et al, EMBO J. (1986) 5: 719–724.

The sequences including the DNaseI hypersensitive sites confer copy number-dependent and position-independent expression upon transgenes (Grosveld et al, 1987; Townes et al, Trends Genetics (1990) 6: 219–223; Bonifer et al, EMBO J. (1990) 9: 2843–2848). The mechanism of action of these sequences, or locus control regions (LCR), is not well defined, but they may help establish a chromosomal domain that facilitates transcription of genes from adjacent chromosomal effects (Elgin, New Biologist (1991) 3: 37–42; Felsenfeld, Nature (1992) 355: 219–224).

No system has been described however which provides tissue-independent, high-level, copy-number dependent, position-independent expression in mammalian cells and/or transgenic systems, much less such a system which is susceptible to regulation. As a matter of fact, no evidence has been reported that such a system exists. Only the existence of cell type-restricted expression sequences associated with gene clusters involved in developmental differentiation have been reported, e.g. the human β-globin gene cluster, 5'-ε-$^G$γ-$^A$γ-δ-β-3' described by Grosveld et al (WO 89/01517).

SUMMARY OF THE INVENTION

Accordingly, one object of this invention is to provide novel transfer systems, including expression systems, useful for the (regulatable) expression of a gene at a high level in a the host cell, in a tissue-independent, essentially integration-site independent, copy number-dependent manner.

It is another object of the invention to provide DNA sequences for improving expression of transgenes in cells; providing for regulatable expression of transgenes through the use of regulatory elements.

All of these objects of the invention, and other objects which will become apparent from the description of the invention given hereinbelow, have been found by the inventors to be satisfied by using at least part of and/or up to the whole LCRs of vertebrate, preferably mammalian, genes which are expressed natively in at least most vertebrate cell systems, and especially those genes that are regulated by external stimuli (agonists). In preferred and illustrative embodiments at least part of, and/or up to the whole LCRs of the vertebrate (preferably mammalian) metallothionein (MT) genes are used, which genes provide the advantage of inducibility.

In accordance with transfer/expression systems of the invention, the DNA flanking sequences and LCRs may be operably attached to the 5'- or 3'-end, or both, of a cistron, either directly or through an intervening sequence. In a preferred embodiment, two of the DNA flanking sequences and/or LCRs of the invention, which may be independently different or identical, are operably attached to the 5'- and the 3'-end of the cistron, again, either directly or through an intervening sequence.

The cistron, which may either contain introns or no introns, comprises at least (a) a promoter/enhancer DNA sequence(s) and (b) a structural gene that is transcriptionally responsive to the promoter/enhancer DNA sequence. The promoter/enhancer DNA sequence(s) and the structural gene may be either homologous or heterologous to each other.

DETAILED DESCRIPTION OF THE PREFERRED EMBODIMENTS

Figure 1A:
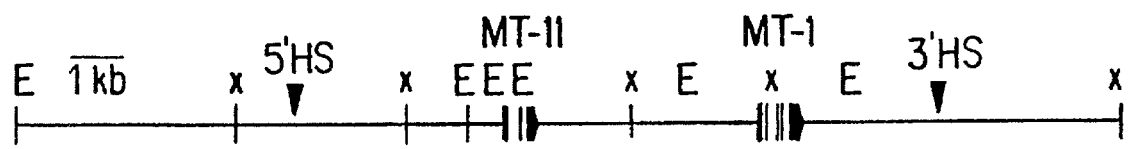
FIGS. 1A and B (FIG. 1 hereinafter) are schematic maps of the mouse MT locus.

The invention relates to the use of DNA flanking sequences and LCRs of vertebrate, preferably mammalian, genes which are expressed natively in at least most (i.e., a plurality of) vertebrate, preferably mammalian, cell systems to confer essentially tissue-independent, integration site-independent, copy number-dependent expression characteristics to a linked gene expression system. The MT-I and -II genes are illustrative of such cell system-independence expression, i.e., expression in a plurality of cell systems. DNaseI hypersensitive site(s) regions within these LCRs have been found to be highly preferred for this high level expression. In a particularly preferred embodiment, the LCRs and DNA flanking sequences of genes that are normally expressed in most vertebrate cells and regulatable are used.

Part of the LCRs, which can be used in accordance with the invention, are referred to in this text as "DNA flanking sequences". DNA flanking sequences used in accordance with the invention should preferably be of a length sufficient to confer to a cistron, when operably linked thereto, essentially tissue-independent, copy number-dependent, position-independent expression. Such sufficient length is generally at least about 300 bases. However, there may be several similar regulatory elements with partial LCR function and they may be separated from each other and the gene they regulate by distances of 1 to 50 kilobase (kb) pairs. The LCRs are likely to be associated with at least one DNaseI hypersensitivity site and they should generate such DNase sensitivity after gene transfer.

In accordance with the invention, the DNA flanking sequences and LCRs are used in conjunction with known transfer expression systems to obtain full expression of genes of natural or synthetic origin, or a combination of the two, in host cells (including those in transgenic animals), providing for the expression of cistrons which can be either homologous or heterologous to the host system and/or to the LCRs and DNA flanking sequences.

The LCRs heretofore described differ from the DNA flanking sequences and LCRs of the present invention in several significant ways, including both function and structure. Know LCRs confer position-independent and copy-number dependent expression of a transgene in a cell-specific manner that differs from the present DNA flanking sequences and LCRs. More particularly, the LCR from the human β-globin gene functions only in the erythroid cells, the LCR from chicken and human lysozyme, only functions in myeloid cells, and the LCR from the CD2 locus expresses that protein specifically in T cells. In contrast, the present DNA flanking sequences and LCRs have been found to confer increased levels of expression of transgenes in many cells types. Thus, the present DNA flanking sequences and LCRs are capable of acting in a more ubiquitous manner in host cells and in transgenic animals.

Furthermore, except for *Grosveld et al* (1987) who reported using globin LCR with TK and neomycin resistance genes in MEL cells, earlier LCR reports did not address manipulating different promoter/enhancer regions with the LCR of interest to obtain improved expression of a targeted transgene. The earlier-described LCRs thus differ significantly from the present DNA flanking sequences and LCRs which function effectively with several heterologous promoter/enhancer sequences, such as elastase and albumin promoter/enhancer sequences.

DNA flanking sequences and LCRs of any vertebrate, and preferably of any mammalian species, can be used in accordance with the present invention, including illustratively, the DNA flanking sequences and LCRs of the following species: humans, primates, agricultural animals such as ruminants (e.g., cattle), fowl (e.g., chickens, turkeys), horses, donkeys, swine, etc., rodents (e.g., rats, mice, etc.), fish, etc.

As used herein, the term "DNA flanking sequences" refers to DNA sequences flanking the gene loci and which include the LCRs. Although these flanking sequences vary somewhat from species to species, they typically comprise one or more DNaseI hypersensitivity sites and lie roughly within 20 kb of the genes themselves. Illustratively, FIG. 1 sets forth the mouse MT locus on chromosome 8, showing the MT-I and MT-II genes separated by about 6 kb, and the DNA flanking sequences containing DNaseI hypersensitivity sites (5'HS and 3'HS).

As of the writing of this document, the term "locus", as in LCR, is a term whose definition is undergoing evolution in the art, and which consequently may be currently viewed by some as being somewhat vague. It can be anything from a single-base pair to a large region. The term literally means location, which can be precise or general. For example, one refers to the β-globin locus, meaning all the globin genes clustered together on the same chromosome but not the β-globin genes which are on a different chromosome. However, one can also refer to the sickle cell locus, meaning the base pair that is mutated in the globin gene responsible for sickle cell anemia. The term "locus control region" has been adopted only recently and undoubtedly will become more refined as its function becomes better understood.

Figure 2:
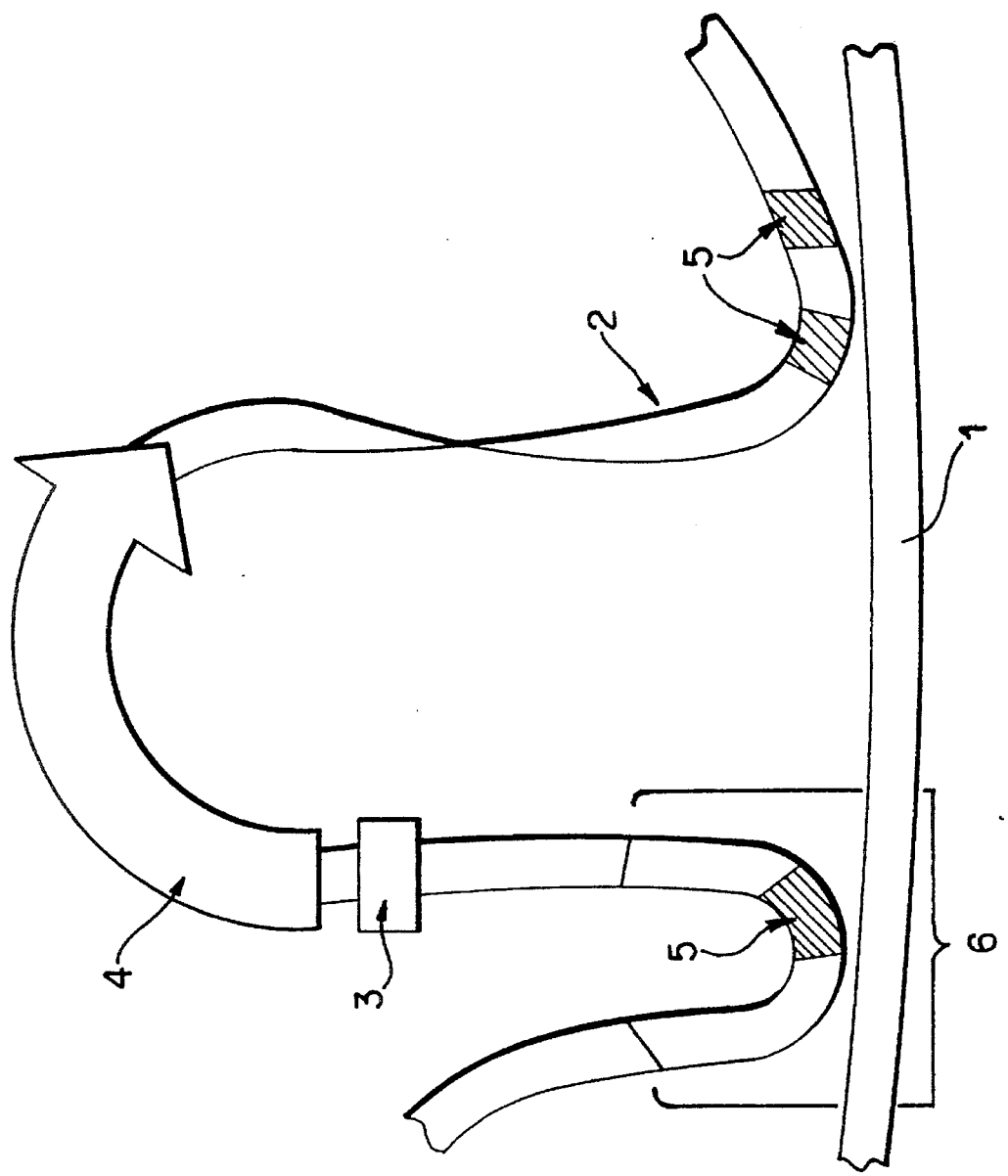
FIG. 2 is a schematic illustration of the inventors' current theory of how the locus control regions may establish a locus "domain". 1 is the nuclear matrix, 2 is a portion of DNA contained in a chromosome, 3 is a promoter/enhancer, 4 is a gene, 5 are DNase I hypersensitivity sites which may also be matrix attachment sites, and 6 is a locus control region. (No relative dimensions are intended to be shown.)

The locus control region (LCR) is meant to be understood by the inventors, as it is used in this text, as playing a role in establishing a chromosomal domain. One domain may be separated from another by physical attachment of the DNA to the nuclear matrix by so-called matrix attachment sites (or MARs). The DNase hypersensitive sites reflect the binding of proteins to the DNA. These proteins may be transcription factors, proteins that also interact with the matrix, or apparently both, as illustrated in FIG. 2. The attachment to the nuclear matrix may be the means of preventing interaction of one domain with another; thus, this may be part of the mechanism of providing copy-number dependent and position-independent expression.

For purposes of the present document, the LCR, from any species, is defined as all the DNA between the genes that are regulated coordinately and neighboring genes that are regulated independently. This can be illustrated as follows:

gene A - gene X - gene B
or
gene A - gene X . . . gene Y - gene B, wherein the LCR for gene(s) X (and Y, if there is more than one gene regulated coordinately) lies within the dashed regions between independently controlled genes A and B. In accordance with the invention gene X (and gene Y) represents an MT gene(s). The intervening distance (the dashed regions in the above illustration) of these systems may be as short as a few hundred base pairs or up to several hundred kilobase (kb) pairs.

At present, it is believed by the inventors that the more important elements of the LCRs used in accordance with the invention lie within approximately 20 kb of the genes, either 5', 3' or both, to the genes. The DNA flanking sequences of the invention are found in, and form part of the LCRs. They comprise at least one DNaseI hypersensitivity site. In this form they are able to confer to a cistron essentially tissue-independent, copy number-dependent, position-independent expression.

In a preferred embodiment, the DNA flanking sequences and LCRs which are used are the MT DNA flanking sequences and LCRs, and in a most preferred embodiment, the DNA flanking sequences and LCR which are used are those of the MT genes that are expressed ubiquitously (thus excluding, for example, the MT-III gene that appears at present to be expressed only in astrocytes, vide infra).

The MT genes of mouse, rat, human, sheep, chicken and fish have been described in most detail in the literature. The mouse and rat gene organizations appear to be similar, so far. The human MT locus is different in that there are 14 MT genes (1 MT-II and 13 MT-I genes) within about 80 kb on human chromosome 16 (*West et al, Genomics* (1990) 8: 513–518).

In their research, the inventors have discovered two more MT genes that are linked to the MT-I and II on mouse chromosome 8. The MT-III gene, which is about 20 kb upstream (5') of the MT-II gene, and the MT-IV gene, which is about 38 kb upstream of the MT-II. In one sense, all four genes constitute the locus. However, the MT-III and IV genes are regulated very differently from the MT-I and MT-II. For example, MT-III is expressed only in the brain (probably in astrocytes). Thus, as a working hypothesis, the inventors suspect that MT-I and MT-II are in one chromosomal domain and that the others are in separate domains. In this hypothesis, the MT-I and II genes are regulated coordinately because they are in the same domain. Humans also have MT-III and MT-IV genes that are about 20 kb apart and closely linked to the other MT genes.

DNA flanking sequences and LCRs useful in accordance with the invention may be cloned, using known recombinant DNA techniques, from naturally occurring vertebrates, preferably mammals, and optionally modified. Useful DNA flanking sequences corresponding to naturally occurring genes may also be manufactured using known techniques of polynucleotide synthesis from sequence data derived from mammalian gene systems. The exact sequences found in any natural LCR may be subject to extensive substitution of one nucleotide for another without altering the LCR function.

Vertebrate, preferably mammalian, MT-DNA flanking sequences used in accordance with the invention should preferably comprise one or more of the DNaseI hypersensitive sites (HS) found naturally adjacent to the MT genes, with each HS being surrounded by as little as 50 bp or up to 20 kilobase pairs of flanking sequences. Either the 5' or 3' MT flanking regions can be used, but in a preferred embodiment the expression system contains both the 5' and the 3' MT flanking regions.

In other embodiments of the invention, the LCRs and DNA flanking sequences of the MT-III, tyrosine aminotransferase (TAase) and/or an acute-phase response protein ($\alpha$-acid glycoprotein, c-reactive protein, hemopexin, fibrinogen, haptoglobin, $\alpha_1$-major-acute-phase protein, serum amyloid A, and $\alpha_2$-macroglobin) genes are used.

These genes also provide the advantage of inducibility, but their use is probably restricted to astrocytes for MT-III and to liver cell systems for the other two. TAase gene expression is responsive to cAMP and glucocortocoids. A TAase gene from liver has been described in detail (*Nitsch et al, Mol. Cell. Biol.* (1990) 10(7):3334–42). Expression of the acute-phase response proteins ($\alpha_1$-acid glycoprotein, C-reactive protein, hemopexin, fibrinogen, haptoglobin, $\alpha_1$-major-acute-phase protein, serum amyloid A, and $\alpha_2$-macro globulin) has been shown to be regulatable with turpentine, (bacterial) endotoxin, lipopolysaccharides, theoglycollate, azocasein, as well as other external factors (for reviews see Kushner, I., *Ann. N.Y. Acad. Sci.* (1982) 389: 39–48; *Koj, A.* In "Structure and function of plasma proteins", (1986), vol. 1, Plenum Publishing Corp., London, p. 73–125; *Gauldie et al, Ann. N.Y. Acad. Sci.* (1989) 557: 47–59).

It is hypothesized at present by the inventors that one of the effects of the DNA flanking sequences is to create a chromosomal domain, so that the promoter/enhancer regions can be recognized by transcription factors regardless of the presumably random sites of chromosomal integration, and, furthermore, that the flanking sequences may protect the transgenes from interference by adjacent transgenes or neighboring chromosomal DNA.

Transgenes containing the present LCRs and/or DNA flanking sequence may be expressed in any suitable animal organs. Furthermore, such transgenes, which may be equipped with an appropriate promoter/enhancer DNA sequence, can be made to respond to external factors (i.e., they may be regulated by external stimuli (agonists)). For example, heavy metal ions (e.g., cobalt, nickel, copper, silver, gold, zinc, cadmium, mercury or bismuth ions) and steroids (including glucocorticoids such as dexamethasone, and probably, projestins and androgens) and (bacterial) endotoxins (such as lipopolysaccharides (LPS)), or cytokines such as IL-1 and IL-6 (*Gauldie et al, Ann. N.Y. Acad. Sci.* (1989) 557: 46–59) can be used by including the MT promoter in the construction. See, *Durnam et al, J. Biol. Chem.* (1981) 256: 5712–5716; *May et al, J. Biol Chem.* (1981) 256: 2621–2624; *Hager et al, Nature* (1981) 291: 30–34. The MT gene is regulated by endotoxin in many cell types (De, McMaster and Andrews, *J. Biol. Chem.*, 1990). If liver-specific expression is desired, then the MT 5'/3' flanks can be used with the albumin promoter (example 13, part D).

The transfer/expression systems which can be used with the invention include, in a broad sense, any composition capable of transferring DNA, susceptible to expression, into a cell or from one cell to another, where the transferred DNA contain at least one mammalian DNA flanking sequence or LCR of the invention operably linked to a cistron. The DNA flanking sequence/cistron or LCR/cistron assembly may contain linkers for ligation into a vector for replication purposes or may be provided with sequences at one or both ends to assist integration into a genome.

Illustratively, the transfer/expression system may be an expression vector, such as a single piece of DNA in linear or circular form and may include, in addition to the DNA flanking sequence(s) of the invention, a cistron operably linked to other known sequences as necessary. For example, the vector may contain additional features such as a selectable marker gene or genes, and/or features which assist translation or other aspects of the production of a cloned product.

The transfer/expression system may alternatively be a cloning vector, suitable in the form of a plasmid, comprising the DNA flanking sequence(s). Such vectors are useful in the construction of vectors for integration.

In accordance with an embodiment of the invention, it is possible to use homologous recombination in embryonic stem (ES) cells to introduce any expression system in accordance with the invention into the (MT) gene locus, either retaining the MT promoter or replacing it with a promoter of choice. This allows utilization of all of the DNA flanking sequences plus additional DNA flanking sequences, if desired. The ES cells may then be used to derive animals with the gene of interest inserted into the MT gene locus with attendant regulation by metals, steroids and/or endotoxins (plus anything else that regulates the gene LCR). (See *Capecchi, Science* (1989) 244: 1288–1292, generally.)

Cistrons which may be used in accordance with the invention include all cistrons falling within the generally accepted definition of the term, which denotes a DNA sequence comprising a promoter/enhancer sequence and a structural gene which is transcriptionally responsive to the promoter/enhancer sequence. Suitable cistrons may contain introns or no introns. The structural gene and promoter/enhancer may be heterologous or homologous to each other and/or to the host. The structural gene and promoter/enhancer may be directly adjacent to each other or may be separated by intervening non-functional sequences.

The promoter may be any promoter capable of functioning in the host cell, for example a mammalian or viral promoter. Optionally, the promoter may be homologous with the gene locus of the DNA flanking sequence and may optionally be present in tandem with another promoter and may optionally include one or more enhancer elements.

The transfer/expression systems of the invention may be used in a host cell; a cell in culture, a cell or tissue added to a multicellular organism (as in gene therapy), or in gene and/or somatic cells of a transgenic animal. Host cells which may be used with this invention include any cell which is susceptible to uptake of a DNA sequence of the invention. The host cell may be obtained from any multicellular eukaryotic organism, a host, which undergoes syngamy, for example, sexual reproduction by the union of gametes. Examples of such organisms include amphibians, reptiles, birds, mammals, boney fishes, cartilaginous fishes, cyclostomes, arthropods, insects, mollusks, thalophytes, embryophytes including gymnosperms and angiosperms. Most preferably the organism is a mammal, including humans, ruminants and rodents. The expression systems of the invention is the host cell may also be regulated by external factors, although it need not be.

The transfer/expression systems may be transferred to the host cell by any known means, such as transfection, infection, microinjection, cell fusion, or protoplast fusion. In a preferred embodiment, the DNA sequence is transferred to the host cell after fusion of the gametes and prior to division of the zygote. If the exogenous genetic material is added after mitosis or cellular division of the zygote, the exogenous genetic material may be added to each resulting nucleus. The DNA sequence may be added to either the male or female pronucleus of the zygote. More preferably, it is placed in either the male or female pronucleus as soon as possible after the sperm enters the egg. The male pronucleus is the preferred site for addition of the DNA sequence of the present invention.

Suitable structural genes usable in the expression systems of the invention may encode a polypeptide which is commercially useful, such as a pharmaceutical, and which may be partially or entirely heterologous to the host cell or host animal. Illustrative examples of such proteins include hormones such as growth hormone, proinsulin, insulin, erythropoietin, blood coagulation factors such as factors VIII or IX, or enzymes such as adenosine or deaminase. Other suitable genes may encode a polypeptide which is deficient or absent or mutated in the host cell or host animal, or a polypeptide having therapeutic value towards a particular condition of the host, including diseases and genetic disorders.

The present invention has very broad uses, spanning from the study of various aspects of genetic development in physiology to commercial use, such as transgenic domestic animals engineered to produce copious amounts of proteins of economic value, such as in the milk, blood or another specific tissue.

The present invention may also be useful for applications in gene therapy. Current strategies involve use of retroviral vectors which can only accommodate limited amounts of DNA (about 6 kb or so) which would preclude the entire 17 kb described herein. However, as the LCR elements become defined they might fit within a retroviral vector. Alternatively, other viral vectors are being developed (e.g., adenovirus) that can accommodate much larger regions of DNA. Finally, improved techniques for transferring DNA into cells without use of viruses are being developed. Thus, it may be possible to efficiently introduce the constructs described herein by one of these methods. The LCR sequences would be ideal for obtaining regulated expression, and they would be particularly well suited for expression in liver, and perhaps also in other cells, e.g., muscle and bone marrow derived cells.

The term "biologically free" is used in this text to describe a material outside of its natural biological environment.

Having generally described this invention, a further understanding can be obtained by reference to certain specific examples which are provided herein for purposes of illustration only and are not intended to be limiting unless otherwise specified.

To date, the best expression achieved by the inventors has been with both a 10 kb fragment from the 5' side of the MT-II gene and a 7 kb fragment from the 3' side of the MT-I gene.

EXAMPLE 1

Construction of a Transgene

Figure 1B:
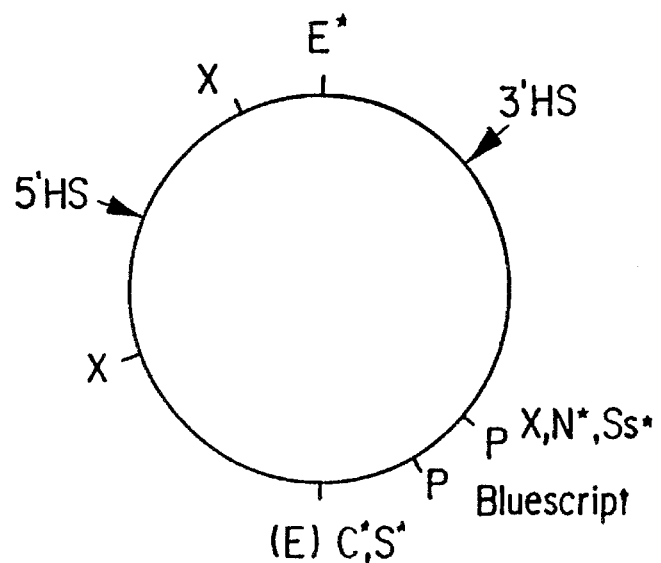

An expression vector was created by subcloning the 5' 10 kb EcoRI fragment and the 3' 7 kb EcoRI-XbaI fragment into Bluescript, to create the MT 5'/3' vector shown in FIG. 1. The MT 5' and 3' flanking regions were initially isolated as EcoRI fragments from lambda phage that had been isolated using mouse MT-I or MT-II gene probes. The unique BglII site in the 4 kb EcoRI fragment containing the MT-I gene (FIG. 1) was converted to an EcoRV; the resulting marked MT gene (mMT-I*) has an additional 2 nucleotides located 9 nucleotides upstream of the translational initiation codon.

The MT-I* gene was made by subcloning the 4 kb EcoRI fragment containing the MT-I gene, digesting to completion with BglII, and then filling in the ends with DNA polymerase using only the first 3 deoxynucleotides. After treating with S1 nuclease, the DNA was ligated and bacteria were transformed. The EcoRI fragment containing the marked MT-I* gene was then cloned into the EcoRI site of the MT 5'/3' vector in the normal orientation. An alternative view of these manipulations is that the 3 EcoRI fragments surrounding the mMT-II gene were deleted from the locus and 2 bp were inserted into the mMT-I gene. All of the other transgenes that were tested in the context of MT 5'/3' sequences were either engineered to have EcoRI or NotI sites at their ends for insertion into the vector, or they were inserted into the EcoRI or NotI sites using adapter oligonucleotides.

EXAMPLE 2

Insertion of Transgene in Transgenic Mice

The transgenes were excised from the Bluescript vector prior to injection with the exception of MT 5'/3' MT-I* and MT-I*, in which 150 and 225 bp of vector were retained to facilitate identification of transgenic mice. After digestion and electrophoresis, DNA was recovered from agarose by a variety of different methods, dissolved in 10 mM Tris-Cl, 0.25 mM EDTA and the concentration determined by fluorescent dye (H33258) binding. DNA was diluted to 2 ng/μl for injection in fertilized eggs derived from mating F1 C57BL/6×SJL females with F1 C57BL/6×SJL males (*Brinster et al,* 1985).

For a typical experiment, about 30 C57/BL6×SJL hybrid females were hormonally superovulated and mated with C57×SJL hybrid males. For some experiments eggs and sperm were from C57/BL6 inbred mice. The next morning, fertilized one-cell eggs were flushed from the oviduct with modified Brinster's medium containing 0.1 mM EDTA. Cumulus cells were removed from the eggs with hyaluronidase (300 units/ml); then the eggs were washed free of debris and enzyme. For injection, the eggs were transferred to a depression slide in Brinster's medium modified by substitution of 25 mM Hepes buffer (pH 7.4) for the bicarbonate and inclusion of cytochalasin B (5 μg/ml). The medium was overlaid with silicone oil [Dow Corning 200 Fluid, 50 centistokes (1 centistoke = $10^{-6}$ m$^2$/sec)]. Eggs were sequentially held in place by a blunt pipet (outside diameter, ≈30 μm) while the tip of the injector pipet was inserted through the zona pellucida and vitellus and into one of the pronuclei. The DNA solution in the injector pipet was slowly discharged (≈2 pl) by using a 100-μl Hamilton syringe connected to a micrometer. The injector pipet was filled with silicone oil except for the DNA solution. After injection the eggs were washed free of cytochalasin B and transferred to the oviducts of pseudopregnant, random-bred Swiss mice.

A convenient assay for successful pronuclear microinjection is to inject a plasmid containing a transcriptionally active gene and assay its expression after incubation for 16–24 hr. We have successfully used the thymidine kinase gene from herpes simplex virus as well as metallothionein-thymidine kinase and metallothionein-β-galactosidase fusion genes for this purpose. Activity assays for these gene products are sensitive enough to detect expression from a few hundred gene copies injected into a single egg. Toxicity studies were conducted by incubating the eggs for 4 or 5 days in Brinster's medium and counting the number that develop to the morula and blastocyst stage.

The following mouse lines were created using vectors created from constructs containing appropriate LCR-promoter sequences. MT 5'/3'-mouse MT LCR; MT-mouse <T' rGHΔi—rat growth hormone (intronless); MT-I*-mouse marked MT; hGH (−83)-truncated human growth hormone.

| Construct designation | Line | Transgene copy number | Code Name | |
|---|---|---|---|---|
| MT 5'/3' —MTrGHΔi | 3439-1 | 3 | Tg (Mt-1, GH) Bri 162 | |
| MT 5'/3' —MT—I* | 3926-1 | 5 | Tg (Mt-1) Bri 172 | |
| MT 5'/3' —MT—I* | 3928-3 | 37 | Tg (Mt-1) Bri 173 | |
| MT 5'/3' —MT—I* | 3962-1 | 56 | Tg (Mt-1) Bri 174 | |
| MT—I* | 4133-5 | 9 | Tg (Mt-1) Bri 185 | |
| MT 5'/3' hGH (−83) | 4249-1 | ND | Tg (Mt-1, GH) Bri 186 | |

EXAMPLE 3

Identification of Transgenic Mice

For routine detection of mice that had integrated the injected DNA, fetal or tail tissue (50–100 mg) was homogenized with a Tissumizer (Tekmar, Cincinnati, Ohio) in 4 ml of SET buffer (1% sodium dodecyl sulfate/10 mM Tris.HCl/5 mM EDTA, pH 7.5) containing 100 µg of proteinase K per ml, incubated for 2 hr at 37° C., and then incubated at ambient temperature for another 24 hr. Then 0.1 ml of 5M NaCl was added, the sample was centrifuged for 10 min at 4000×g, and an aliquot (0.4 ml) was mixed with 0.8 ml of ethanol and incubated overnight at −20° C. The nucleic acids were collected by centrifugation for 1 min at 15,000×g and dissolved in 15 µl of 2M NaCl/0.1M HaOH by heating in a boiling water bath for 1–2 min. The sample was centrifuged briefly and mixed gently in a Vortex, and 5 µl was spotted directly onto nitrocellulose (Sartorius). The pipet tip was rinsed with ethanol prior to picking up the sample to facilitate sample dispersion on the nitrocellulose. After air drying, the nitrocellulose was washed briefly in 0.30M NaCl/0.03M sodium citrate, pH 7, and baked for 2 hr at 80° C. The filters were hybridized with a probe corresponding to the small piece of Bluescript that was left on the injected DNA, washed, and exposed to x-ray film as described. This procedure results in about 2–5 µg of DNA being spotted on the nitrocellulose, which is sufficient to detect single-copy inserts with an overnight exposure. For quantitation, nucleic acids were isolated; then known amounts of DNA were spotted along with plasmid standards and hybridized as above. Five transgenic founder mice were identified by dot hybridization using this technique. Transgene copy number was determined by spotting known amounts of DNA from 3 to 5 separate mice on duplicate nitrocellulose filters and hybridizing one with a probe corresponding to the mMT-I promoter region and the other with a unique probe from the Hox 1.4 locus. The ratios of radioactivity hybridized to each dot (determined by scintillation counting) were compared to the ratios of nontransgenic controls to establish transgene copy number. Southern blots allowed visual comparison of the transgene copy number with that of the endogenous genes and the results confirmed those obtained by quantitative dot hybridization.

EXAMPLE 4

Expression of Transgene

Figure 3:
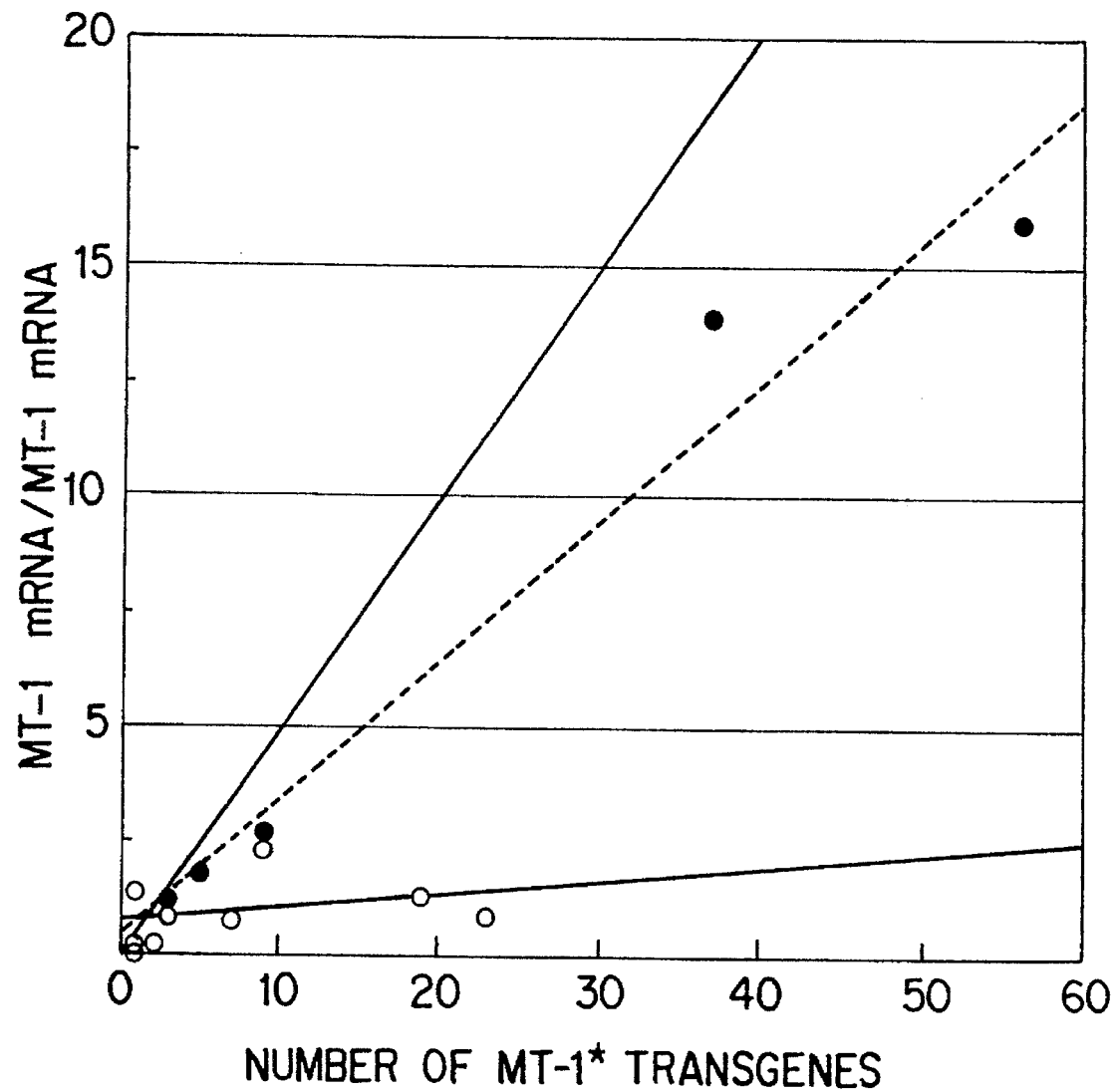
FIG. 3 is a graph which relates the number of copies of MT-I* (a marked metallothionein gene) to the amount of MT-I* mRNA/MT-I mRNA isolated from liver tissue.

The five mice obtained in Example 3 were bred to establish lines. The founders and their offspring were exposed to zinc in their drinking water for 6 days prior to partial hepatectomy. MT-I and MT-I* mRNAs were measured by solution hybridization using oligonucleotide probes complementary to the region that was mutated (see Example 5 oligonucleotides MT 343 and MT 353). To establish conditions under which there was no cross hybridization, these probes were tested with nucleic acid samples containing only MT-I or MT-I* mRNA made in BHK cells that were transfected with constructs containing MT-I or MT-I* genes cloned into pNUT, a high copy number expression vector. MT-I gene copy number was determined by quantitative DNA dot hybridization by making duplicate filters of DNA samples and hybridizing one filter with a probe corresponding to the mMT-I promoter region and the other with an unrelated unique probe. The ratio of the radioactivity on the two filters was then used to determine the transgene copy number. In FIG. 3, the ratio of MT-I* to MT-I mRNA is plotted relative to transgene copy number. The solid circles represent MT-I* transgene with MT 5'/3' flanking regions. The open circles represent MT-I* transgene without MT 5'/3' flanking regions (see Comparative Example 1). The solid line depict the theoretic ratio expected if expression of each transgene was equivalent to an endogenous MT-I gene. The dashed lines are linear expressions.

The amount of MT-I* mRNA in the livers of the founder mice and several of their offspring was proportional to gene copy number up to 56 copies of the transgene (FIG. 3, dashed line) and close to the theoretical value. The endogenous MT-I mRNA in Zn-induced mice averages about 2500±670 molecules per cell; thus, some of these transgenic mice have about 40,000 molecules/cell of MT-I mRNA which we estimate would represent 10 to 20% of total hepatic mRNA. Because the mutation in MT-I* is not expected to alter mRNA function, these transgenic mice probably make large amounts of MT-I protein. Nevertheless, no ill effects of the transgenes have been noted over several generations of continuous breeding.

Figure 4A:
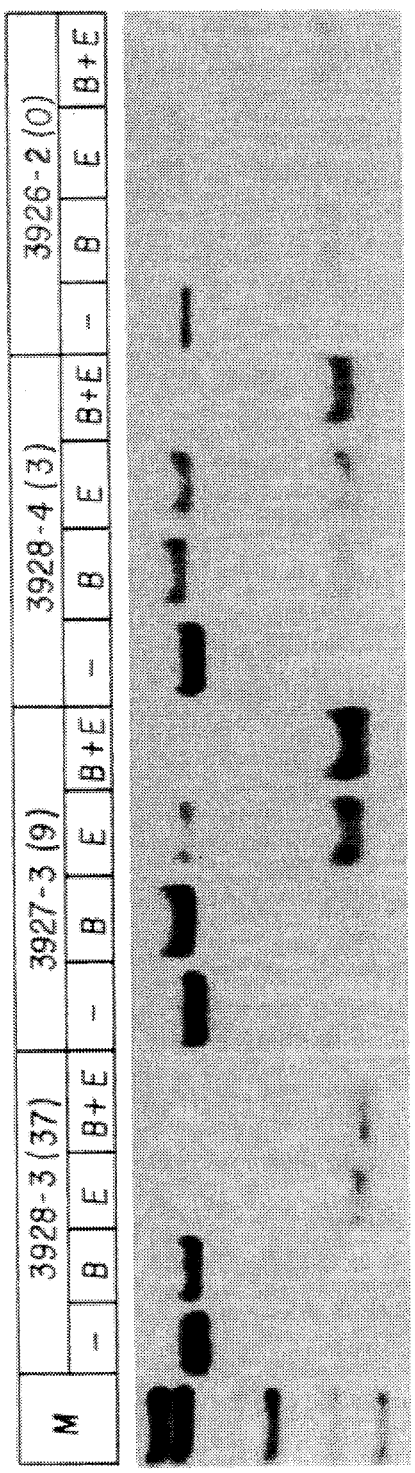
FIGS. 4A and B are photographs of autoradiograms obtaining from polyacrylamide gels of $^{32}$p labelled DNA samples digested with BglII (B), EcoRV (E), both enzymes (B+E) or undigested (−). The gels represented in part A were obtained from transgenic mice with MT 5'/3' flanking sequences. The gels represented in part B were obtained from transgenic mice without these MT flanking sequences.
Figure 4B:
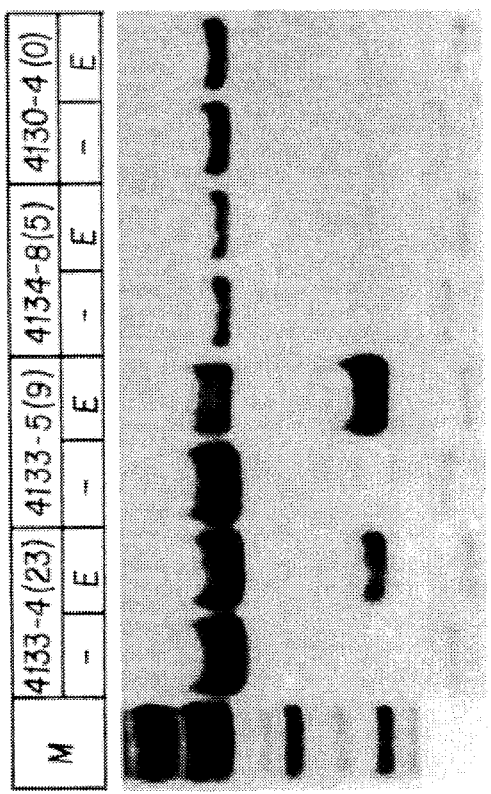

As an alternative means of measuring transgene mRNA, total MT-I mRNA was amplified by RT-PCR using primers that span the 2 bp insertion in MT-I* and the products were restricted with BglII or EcoRV. In this assay, mRNA produced from the transgene is cleaved by EcoRV whereas product from the endogenous mRNA is cleaved with BglII. Samples of liver RNA were amplified using a pair of primers that lie on both sides of the 2 bp insertion in MT-I* transgene. The 3' primer was end-labeled with $^{32}$p prior to PCR. Following amplification, DNA samples were digested with BglII (B), EcoRV (E), both enzymes (B+E) or undigested (−). Samples were then examined after electrophoresis on nondenaturing polyacrylamide gels and autoradiography. Transgene copy numbers are indicated in parentheses. DNA size markers were generated by end-labeling MspI cut pBR322. The full length PCR product is 138 bp (closed triangle), digestion yields a single band of 74 bp (open triangle). Liver mRNA from transgenic mice with MT 5'/3' flanking sequences are shown in FIG. 4A. Liver mRNA from mice without MT flanking regions are shown in FIG. 4B. In B, the MT-I* gene was amplified in a separate reaction and added to the RT-PCR reaction after amplification as in internal control to monitor enzyme digestion (solid circle). Note in part B that if the PCR reaction extends for too many cycles, then heterodimers form which migrate more slowly and will not cut with either enzyme. In this experiment we purposefully used a high cycle number to reveal low abundance MT-I* mRNA.

FIG. 3 shows that amount of total amplification product that was cleaved with EcoRV was proportional to transgene copy number. In the two high-copy lines, almost all of the product was cut with EcoRV.

EXAMPLE 5

Preparation of Oligonucleotides for Solution Hybridization

For solution hybridization the following oligonucleotides were used: MT 57 (complementary to 3' UTR MT-I mRNA); hGH 149 (complementary to 3' UTR of hGH); rGH 150 (complementary to 5' UTR of rGH); MT 343 (complementary to MT-I* with mutation in the middle of the oligo); MT 353 (complementary to MT-I in same region as oligo 343); TGF 287 (complementary to rat TGF-α mRNA). MT 57 is the primer used to make MT-I cDNA, while MT 344 and MT 44 are the 5' and 3' primers, respectively, that were used for PCR.

| | | |
|---|---|---|
| MT 44 | 5' TCTTGCAGGCGCAGGAGCTG | (SEQ ID NO: 1) |
| MT 57 | 5' GAAAACGGGGGTTTAGTAAACAGGG | (SEQ ID NO: 2) |
| MT 343 | 5' CATTCCGAGATATCTGGTGAA | (SEQ ID NO: 3) |
| MT 344 | 5' CACCACGACTTCAACGTCC | (SEQ ID NO: 4) |
| MT 353 | 5' CATTCCGAGATCTGGTGAA | (SEQ ID NO: 5) |
| hGH 149 | 5' GGCTGGTGGGCACTGGAGTGGCAACTT | (SEQ ID NO: 6) |
| rGH 150 | 5' GCATTGGCAAACAGACTGGACAAGGGCAT | (SEQ ID NO: 7) |
| TGF 287 | 5' GCGGGGGAAAAAGGCGCAGGCGACAG | (SEQ ID NO: 8) |

EXAMPLE 6

Quantitation of mRNA

The amount of mRNA was routinely determined by solution hybridization using total nucleic acid (TNA) as described in detail by Durnam et al (*Anal. Biochem.*(1983), 131: 385–393) and modified for oligonucleotides by Townes et al (*EMBO J.* (1985) 4: 1715–1723). Briefly, tissue samples were digested in 1X SET (1% sodium dodecyl sulfate, 20 mM Tris-Cl, 10 mM EDTA) with 100 mM NaCl and 100 µg/ml of proteinase K, then subjected to phenol-chloroform extraction, precipitated with ethanol and dissolved in 0.2X SET. Several aliquots (ranging from 0.1 to 50 µg TNA) were hybridized at 450 overnight with about $10^4$ cpm of end-labeled oligonucleotides in a 30 µl reaction mix. Samples were then diluted to 1 ml with S1 nuclease buffer containing 10–15 units of S1 nuclease, digested for 1 hr at 45° precipitated with 0.6N trichloroacetic acid, collected on GF/C filters, and counted in a Packard scintillation counter. A standard curve was constructed with M13 DNA complementary to the probe. Molecules/cell were calculated using the standard curve and knowing the amount of DNA in each TNA sample. Standards containing only MT-I or MT-I* mRNA were prepared by transfecting BHK cells (which do not express any MT) with MT-I or MT-I* genes cloned into pNUT, a high copy number expression vector.

For RT-PCR, TNA samples were precipitated with ethanol, dissolved in 75 mM KCl, 10 mM Tris-Cl, 4.5 mM $MgCl_2$, 0.25 mM $CaCl_2$, pH 8, digested with DNaseI (1 unit), treated with proteinase K and then boiled to inactivate the enzymes. The primer, deoxynucleotides and reverse transcriptase (2 units) were added and incubated for 30 min at 42° to make cDNA. Aliquots of the cDNA were then amplified by PCR using oligonucleotides 5' and 3' of the EcoRV site in MT-I*.

COMPARATIVE EXAMPLE 1

Transgenic Mice Lacking MT Flanking Sequences 10 transgenic mice with MT-I* gene lacking the MT flanking sequences were produced using analogous methods to Examples 1 and 2. These founder mice were treated with Zn and liver biopsies were used to determine total MT-I mRNA levels and transgene copy numbers as above. The amount of MT-I* mRNA ranged from undetectable (as revealed by solution hybridization and RT-PCR) to values that were equivalent to endogenous MT-I; the average amount of MT-I* mRNA was about 6-fold lower than the previous construct which contained MT flanking sequences. We conclude that the inclusion of the MT 5'/3' flanking regions confers a remarkable degree of copy number dependency on expression of the MT-I* reporter gene. Moreover, because the expression level per transgene is nearly equivalent to that of the endogenous MT-I gene, it is likely that all of the elements necessary for normal levels of hepatic expression are contained within this construct.

EXAMPLE 7

Expression of MT-I* in Various Tissues

Figure 5A:
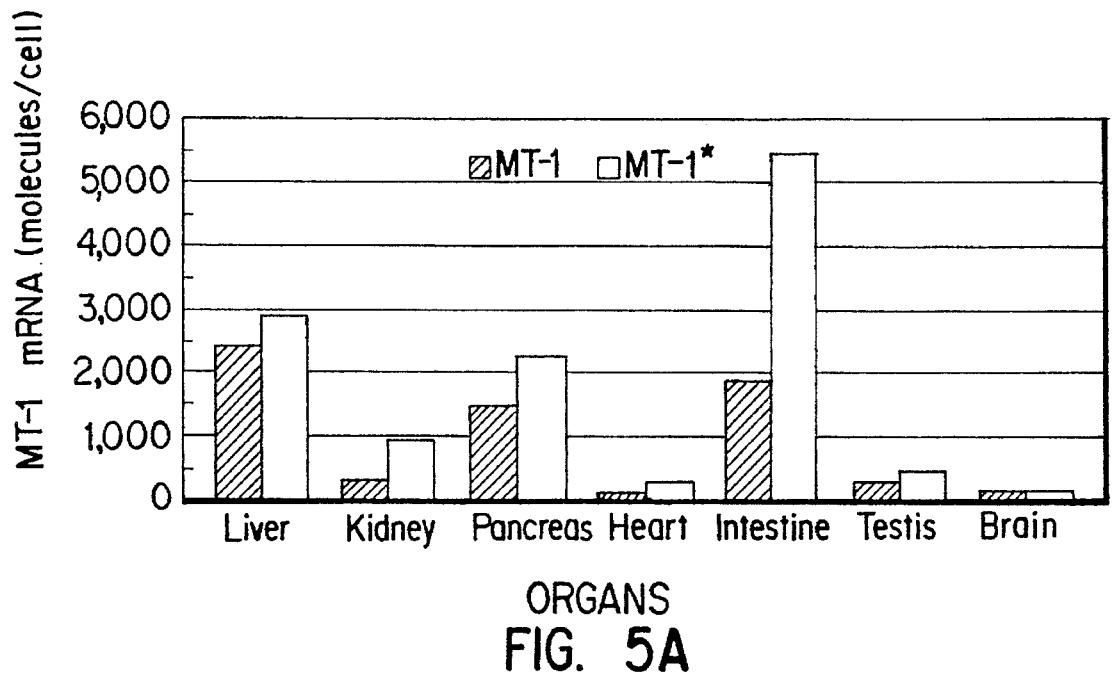
FIGS. 5A and B are histograms representing the expression of MT-I* in various organs. Graph A represents the expression of a transgene containing the MT 5'/3' flanking sequences. Graph B represents the expression of a transgene w/o these MT-flanking sequences.

To ascertain whether the MT-I* transgene flanked by the MT 5'/3' sequences was regulated properly in tissues other than liver, offspring from several lines of transgenic mice with (mouse line 3926-1) or without (mouse line 4133-5) the MT flanking sequences were treated with 25 mM $ZnSO_4$ in their drinking water for 6 days. MT-I and MT-I* mRNAs levels were determined from several organs by solution hybridization. FIG. 5A shows that the ratio of MT-I* to MT-1 mRNA in a mouse with 5 copies of MT 5'/3' MTI* (mouse line 3926-1) was relatively constant in the seven different organs examined, ranging from 1 in the brain to 2.5 in intestine. Other mice within this line were similar and other lines with this construct showed a similar pattern but different ratios, depending on transgene copy number. In contrast, transgenic mice without MT flanking sequences (mouse line 4133-5; contains 9 copies of the MT-I* transgene) showed large variations in the ratio of MT-I* to MT-I mRNA among organs. For example, as shown in FIG. 4B, a mouse with 9 copies of the MT-I* transgene had a ratio of 2 in liver and testis, a very low ratio in pancreas and undetectable levels of MT-I* mRNA in kidney, heart and brain. Similar results were obtained with two other transgenic lines with this construct.

EXAMPLE 8

Regulation of Transgene with External Factors

The acute response of liver and other organs to cadmium, dexamethasone and lipopolysaccharide (LPS) was also examined in livers from a transgenic line (mouse line 3928-3) carrying 37 copies of the MT 5'/3' MT-I* transgene. Mice were either untreated, maintained on 25 mM $ZnSO_4$ in their drinking water for 5–6 days, injected with $CdSO_4$ (1 mg/kg, intraperitoneal), or injected with lipopolysaccharide (Sigma). Mice were killed after 5–7 hr after injections and total nucleic acids were isolated from liver for mRNA analysis by solution hybridization. These results are summarized below. The numbers in parentheses indicate the number of liver samples analyzed.

|  | Transgene | | |
|---|---|---|---|
| Treatment | None | MT5'/3' MT—I* mRNA molecules/cell | MT5'/3'MTrGH |
| none | 920 (10) | 9,450 (3) | 1,280 (3) |
| ZnSO$_4$ | 2,500 (5) | 37,000 (3) | 10,100 (4) |
| CdSO$_4$ | 5,950 (3) | 68,900 (1) | 2,900 (1) |
| Dexamethasone | 3,600 (3) | 78,600 (2) | 4,800 (4) |
| Endotoxin (LPS) | 8,740 (2) | 168,000 (2) | ND |

The amount of total MT-I mRNA in liver 7 hr after injection of cadmium, dexamethasone or LPS increased proportionately to that observed in nontransgenic controls and was 12- to 22-fold higher than controls (compared to an expected ratio of 18.5). LPS and dexamethasone gave the best induction and total MT-I mRNA levels reached $10^5$ molecules/cell. Other organs such as kidney, pancreas, intestine and brain also responded to these inducers and the testis was unresponsive as is the case with endogenous MT genes (data not shown). Thus, the MT-I* transgenes appear to respond to developmental, cell-specific and environmental signals in an appropriate manner.

EXAMPLE 9

Responsiveness to Fetal Regulatory Signals

MT-I is naturally induced in fetal liver during development. Therefore, the response of MT-I* to fetal regulatory signals was examined. The livers of fetal and adult mice from six different lines were examined to determine the amount of mRNA molecules per cell. Total MT-I or rGH mRNA was measured by solution hybridization of total nucleic acid isolated from livers of 17-day fetal livers or adult liver of mice reared on ZnSO$_4$ for 6 days. One line of MT 5'/3' MTrGH mice (3439-1) and 2 different lines of mice with the MT-I* (4131-3 and 4133-5) or MT 5'/3' MT-I* (3926-1 and 3928-3) transgene were used; transgene copy numbers are indicated in parentheses. Values are +/− SEM; n=3 to 5 except for two MT-I* adult values where n=1.

| Transgene | Fetal liver | Adult liver (mRNA molecules/cell) |
|---|---|---|
| none | 550 +/− 30 | 2,500 +/− 670 |
| MT 5'/3' MT—I* (5 copy) | 1,530 +/− 205 | 4,900 +/− 950 |
| MT 5'/3' MT—I* (37 copy) | 3,720 +/− 165 | 39,600 +/− 3,850 |
| MT—I* (7 copy) | 705 +/− 25 | 8,360 |
| MT—I* (9 copy) | 550 +/− 35 | 8,280 |
| MT 5'/3' MT-rGH (3 copy) | 150 +/− 20 | 10,100 +/− 1,900 |

EXAMPLE 10

Responsiveness of the MT 5'/3' Flanking Sequence Linked to Heterologous Promoters to Dexamethasone (DEX) and Lipopolysaccharide (LPS)

To ascertain whether the MT 5'/3' flanking regions could confer responsiveness to glucocorticoids and lipopolysaccharide to heterologous promoters, transgenic mice bearing these sequences and either the albumin promoters, transgenic mice bearing these sequences and either the albumin promoter driving expression of TGFa or a minimal hGH gene with only 83 bp of promoter were either untreated or injected with DEX or LPS and liver mRNA was measured 4 to 6 hours later. The table shows that both of these transgenes were induced at least 30 fold by either treatment.

The MT 5'/3' flanking sequences confer responsiveness to dexamethasone (DEX) and lipopolysaccharide (LPS) to heterologous promoters.

| Transgene | Control | DEX-treatment mRNA (molecules/cell)[a] | LSP treatment |
|---|---|---|---|
| MT 5'/3' Alb-TGFa[b] | 580 | 16,080 | 16,225 |
| MT 5'/3' −83hGH[c] | 400 | 12,100 | 30,830 |

[a]TGFa and hGH mRNAs were measured by solution hybridization using oligos specific for these mRNAs and the amount of mRNA per cell was calculated as described in Methods.
[b]The MT 5'/3' Alb-TGFa transgene is described in example 13 below.
[c]The MT 5'/3' −83hGH transgene is described in example 15 below.

Two different transgenic lines with the MT flanking regions showed a significant increase in total hepatic MT-I mRNA at fetal day 17, whereas two lines without the flanking region showed little change compared to littermate controls. These results suggest that the MT flanking regions confer responsiveness to fetal regulatory signals.

EXAMPLE 10

Figure 6:
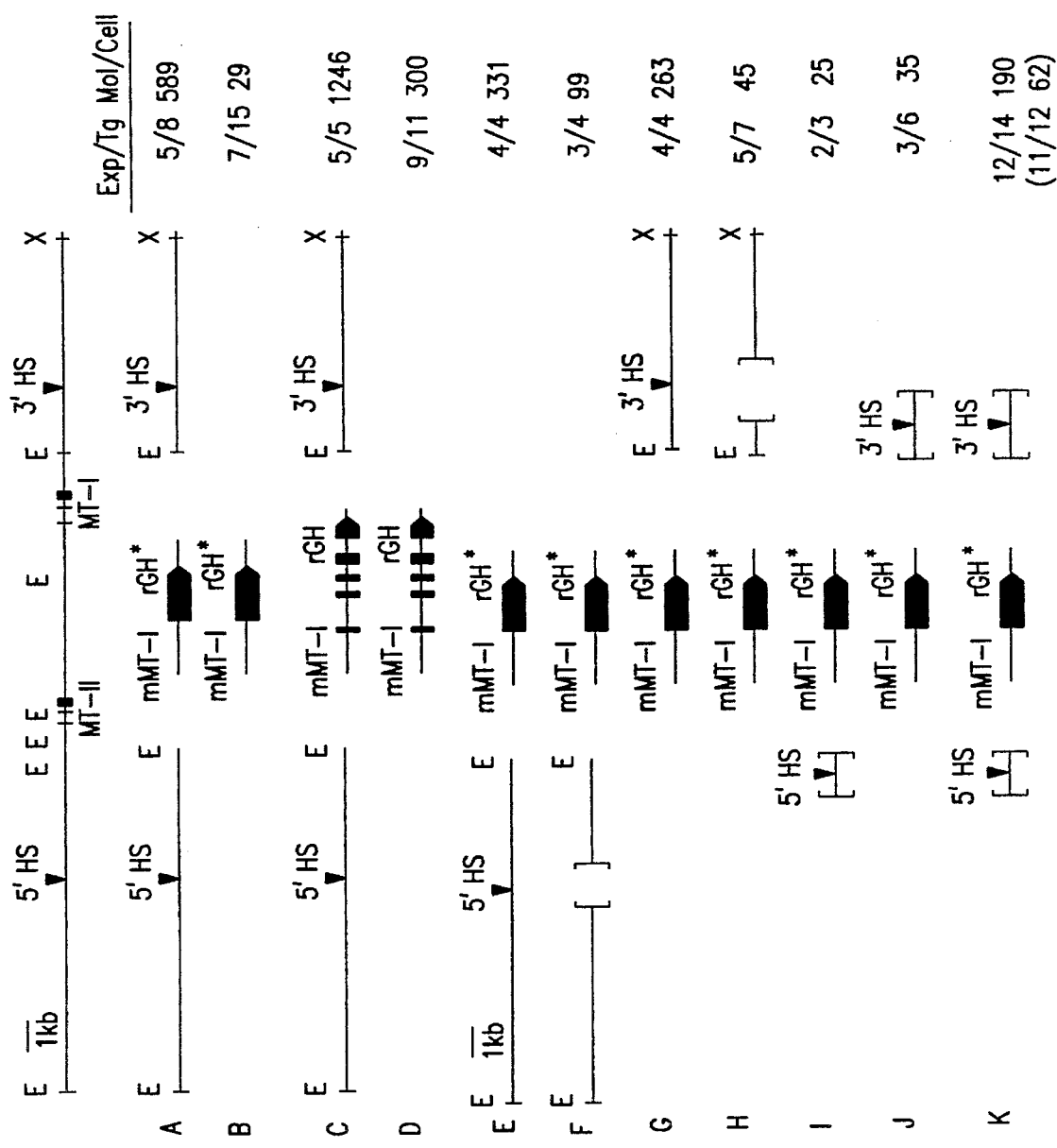
FIG. 6A–K are schematic maps of various MT-rGH genes with various flanking regions.
Figure 7:
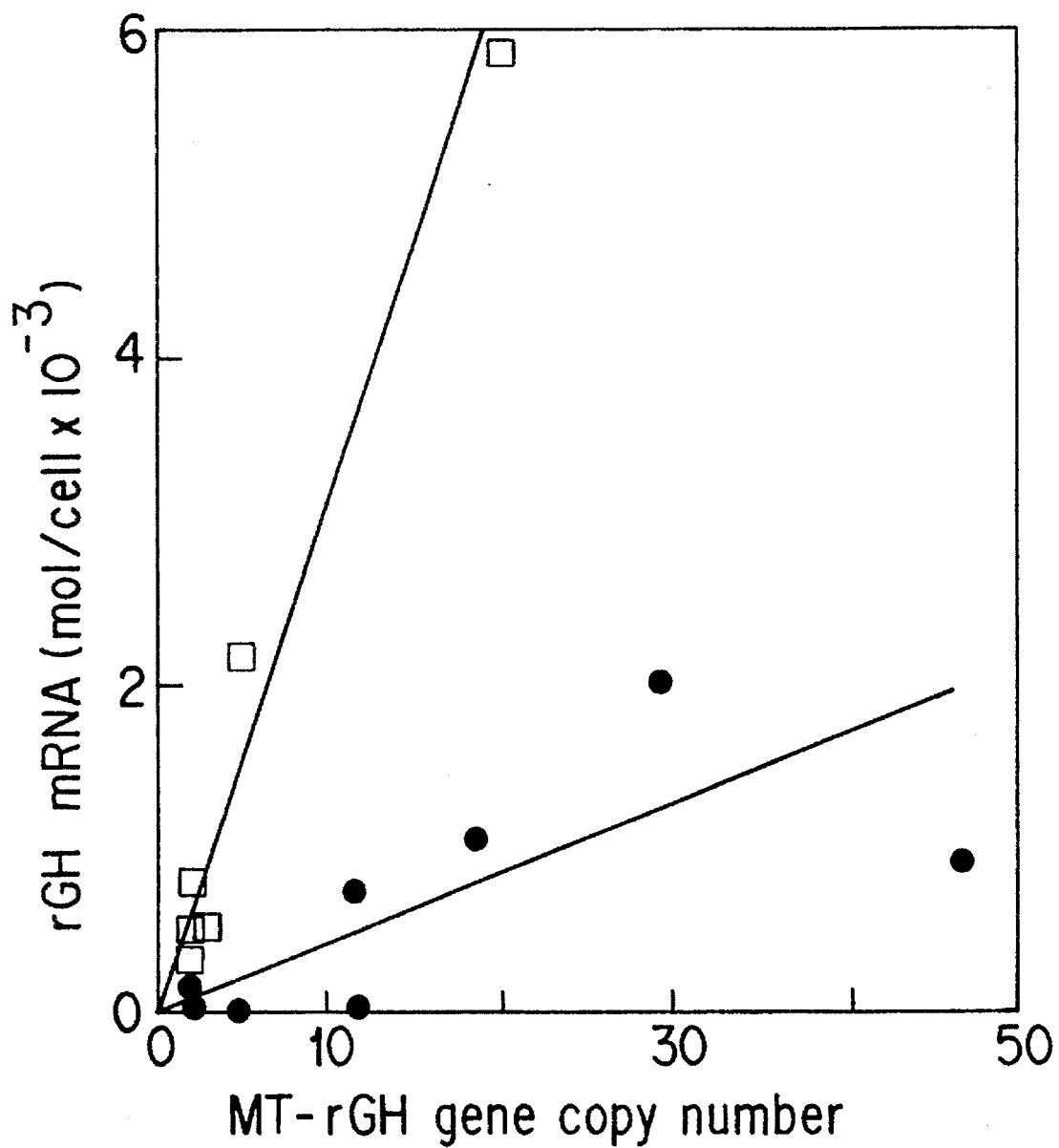
FIG. 7 is a graph which relates the number of copies of a cistron containing MT 5'/3' flanking sequences and a natural rGH gene (open circles) or a intronless rGH gene (closed circles) as a function of the amount of rGH mRNA isolated from fetal liver.

Effect of MT LCR on the Expression of a Heterologous Cistron (MT-rGH) Containing Either a Natural rGH Gene or an Intronless Variant The expression of MT-rGH constructs that contained either the natural rGH gene or an intronless variant, each driven by the mMT-I promoter in the context of the MT flanking regions were tested to determine their ability to express in transgenics. The results were compared with those obtained in a previous study in which the MT flanking regions were not included (*Brinster et al*, Proc. Natl. Acad. Sci. USA (1988), 85: 836–840). The MT-rGH genes were cloned into the EcoRI site of the MT 5'/3' vector in the normal orientation and the vector DNA was completely removed prior to injection into fertilized eggs. Transgene expression was measured in day-17 fetal liver samples by solution hybridization using a probe complementary to the first exon of rGH. FIG. 6A shows that the average level of expression of the intronless MT-rGH gene was 20-fold higher when it was flanked by the MT 5' and 3' sequences than when tested alone FIG. 6B. Expression of the complete rGH gene was also simulated several-fold by including the MT flanking sequences (compare C and D in FIG. 6). The copy number-dependency of this sequence's expression was determined by analyzing the amount of rGH mRNA by solution hybridization using oligonucleotide rGH 150. FIG. 7 shows the gene copy number relationships determined for these MT-rGH transgenes. With the natural rGH gene (solid circles, solid line), all the transgenic mice expressed the transgene and mRNA levels were proportional to gene copy number; however, with the intronless rGH gene (open circles, dotted line), there was good correspondence of expression for most of the mice that expressed the gene, but one mouse with the most transgenes produced about half as much rGH mRNA as the others on a per gene basis and 3 mice failed to express the transgene. Southern blots confirmed the gene copy number determinations and revealed that most, if not all, of the transgene copies were intact.

EXAMPLE 11

Responsiveness of a Construct Containing the 5'/3' MT LCR and a Heterologous Cistron (MT-rGH) Containing an Intronless rGH Gene Four lines of transgenic mice with the construct shown in FIG. 6 (A) were established. Eight offspring were produced which had transgene copy numbers ranging from 3 to 43. Four of these offspring were reared for 6 days with 25 mM $ZnSO_4$ in their water. The other 4 were left untreated. The average level of hepatic expression after Zn induction was 1860±480 mRNA molecules/cell/transgene. Then the total nucleic acids were isolated from the indicated organs and rGH and MT-I mRNA were determined by solution hybridization. The ratio of rGH to MT-I mRNA in the zinc-induced samples is shown in the last column. Similar results were obtained with an MT-rGH transgenic line with 3 copies of the transgene.

| | rGH mRNA (molecules/cell) | | |
|---|---|---|---|
| Tissue | −Zn | +Zn | rGH/MT—I |
| pancreas | 4,280 +/− 1,120 | 21,900 +/− 3,460 | 137 |
| liver | 4,050 +/− 454 | 37,500 +/− 2,750 | 52.2 |
| kidney | 165 +/− 55 | 3,300 +/− 250 | 5.0 |
| ovary | 90 +/− 30 | 430 +/− 23 | 3.8 |
| heart | 88 +/− 9 | 165 +/− 18 | 3.6 |
| intestine | 790 +/− 75 | 4,250 +/− 850 | 2.6 |
| lung | 20 +/− 9 | 25 +/− 14 | ND |

The transgene was induced by zinc treatment to the same extent (5- to 10-fold) in the liver, kidney and intestine as was the endogenous MT-I gene. However, the ratio of MT-rGH to MT-I mRNA varied widely from one organ to another, in contrast to that observed with the MT 5'/3'-MT-I* transgene (FIG. 5A). We also noted a remarkable difference in the ratio of MT-rGH to MT-I when comparing fetal and adult liver values (see Example 9). Because the MT-I promoter and flanking regions are identical to those used in MT-I* construct, the differences in ratios of rGH to MT-I either reflect differences in mRNA stability or differential effects of the rGH gene on the transcription from the MT-I promoter in various cell types.

EXAMPLE 12

Location of Important Control Elements in the MT Locus

To ascertain whether both 5' and 3' MT flanking regions are necessary for efficient transgene expression, we tested them separately with the intronless MT-rGH reporter gene. FIGS. 6E and 6G show that both 5' or 3' MT flanking regions can enhance expression when tested alone, but the average level of expression with either is about half that obtained with both (FIG. 6A). Because the average level of expression is nearly proportional to the length of DNA added to the reporter gene construct, we were concerned that the MT flanking regions might be acting in a nonspecific manner, perhaps as a spacer between the reporter gene and DNA at the site of integration. To test this possibility and determine whether the regions that where shown to be DNaseI hypersensitive in S49 cells were important for expression, we deleted 1.6 to 2 kb of DNA, including the hypersensitive regions, from the constructs described above. In both cases (FIGS. 6F and 6G), expression of the MT-rGH gene decreased 3- to 6-fold, significantly more than would be predicted from a nonspecific decrease in the length of flanking DNA. The results suggest, therefore, that there is a functional element in the region delineated by DNaseI hypersensitive site mapping. However, when small (approximately 1.2 to 1.6 kb) regions containing the hypersensitive sites were tested by themselves they were inactive (FIGS. 6I and 6J). The combination of both of these small 5' and 3' regions with the MT-rGH reporter gene enhanced the average level of expression about 6-fold (FIG. 6K); however, these data are biased by one super-expressor. If one eliminates the highest and lowest values from this data set, then the average level of expression is only twice that of the control lacking both flanking regions (see number in parentheses). In summary, these results suggest that the MT flanking sequences can function independently of each other and that the DNaseI hypersensitive regions are necessary but not sufficient for high-level expression.

EXAMPLE 13

Figure 5B:
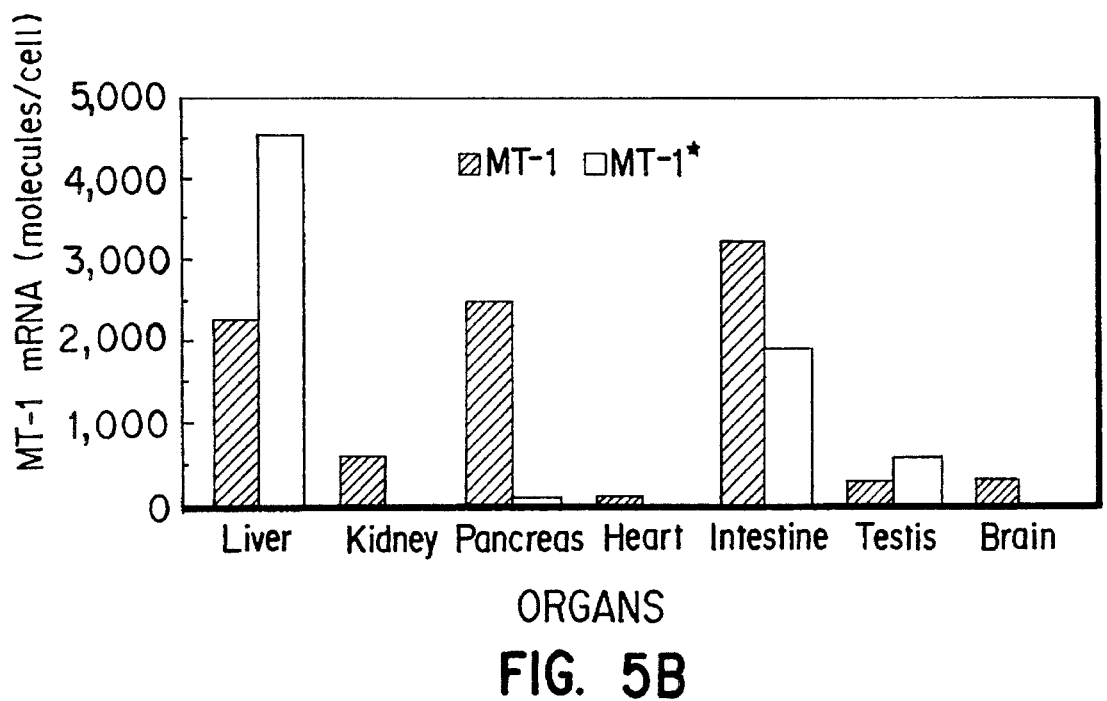

Effect of MT Flanking Regions on Heterologous Cell-Specific Promoter/Regulators In the next set of experiments, we tested the MT flanking sequences in conjunction with cell-specific promoter/regulators from the rat elastase gene, which directs expression of reporter genes to pancreatic acinar cells; the mouse albumin gene which directs expression of report genes to hepatocytes; the rat growth hormone gene, which directs expression of reporter genes to pituitary somatotroph cells; and the mouse protamine I gene, which directs expression of reporter genes to round spermatids. In each case, the promoter/enhancer was fused to the reporter gene indicated and that construct was then separated from the plasmid vector DNA or inserted into the EcoRI site of the MT 5'/3' vector and then separated from plasmid vector DNA prior to microinjection. The rat elastase I- intronless rGH construct is the same as described previously (*Brinster et al*, 1988). The rat elastase I promoter/enhancer was also fused to the mouse urokinase (uPA) gene used previously (*Heckel et al*, Cell (1990), 62: 447–456) or a c-myc gene with a ligand-binding domain of the estrogen receptor (ER) and a hGH 3' untranslated region. The mouse albumin promoter/enhancer (*Pinkert et al, Genes Dev.* (1987), 1: 268–276) was fused to rat TGF-alpha (*Sandgren et al, Cell* (1990), 61: 1121–1230). The mouse protamine I promoter/enhancer (*Peschon et al, Proc. Natl. Acad. Sci. U.S.A.* (1987), 84: 5316–5319) was fused to the mouse protamine I gene with an hGH 3' untranslated region. The rGH-hGH construct is the same as used previously (*Behringer et al, Genes Dev.* (1988), 2: 453–461). Exp/Tg is defined in legend to FIG. 5. The expression (molecules of mRNA/cell) was determined by solution hybridization using labeled oligonucleotides specific for the reporter gene. For elastase constructs, mRNA levels were determined in adult pancreas; the values for the construct without the MT 5'/3' sequences were reported previously (Brinster et al, 1988); the adult and neonatal values were compared after correction for the change in elastase mRNA between the two stages. For the albumin construct, mRNA was measured in adult liver; protamine mRNA levels were measured in adult testis, and the rGH-hGH mRNA levels were assayed in adult pituitary. mRNA was also assayed in the following organs: pancreas, liver, heart, spleen, intestine, testis or ovary, to assess organ-specific expression. The following Table summarizes the expression levels of various heterologous promoter/regulators when combined with both the MT 5'/3' LCR and various reporter genes.

Effects of MT flanking regions with heterologous promoter/enhancers.

| MT locus | Promoter/enhancer | Reporter gene | Exp/Tg | Expression molecules/cell |
|---|---|---|---|---|
| A. MT 5'/3' | rat elastase I | rGH (intronless) | 9/9 | 3,500 |
|  | rat elastase I | rGH (intronless) | 3/17 | 56 |
| B. MT 5' only | rat elastase I | uPA | 6/8 | 780 |
|  | rat elastase I | uPA | 10/22 | 105 |
| C. MT 5'/3' | rat elastase I | myc-ER-hGH | 4/12 | 8 |
|  | rat elastase I | myc-ER-hGH | 3/8 | 13 |
| D. MT 5'/3' | mouse albumin | TGF-alpha | 8/8 | 390 |
|  | mouse albumin | TGF-alpha | 4/16 | 64 |
| E. MT 5'/3' | mouse protamine I | protamine-hGH | 8/8 | 1,020 |
|  | mouse protamine I | protamine-hGH | 2/3 | 2,200 |
| F. MT 5'/3' | rat GH | human GH | 5/5 | 900 |
|  | rat GH | human GH | 4/4 | 6,600 |

In each case, these promoter/enhancers have been shown previously to direct expression predominantly, if not exclusively, to specific cell types. The MT flanking sequences improved expression substantially when tested in conjunction with the elastase promoter/enhancer fused to either the intronless rGH gene or a mouse urokinase (uPA) gene, although it did not have a significant effect on the expression of a modified c-myc gene. The amount of pancreatic rGH mRNA was proportional to transgene copy number from nine MT 5'/3' elastase-rGH mice (about 250 mRNA molecules/cell/transgene) except that two mice had about 6-fold more mRNA than predicted from their transgene copy number. The expression of an albumin-rTGFα was also improved by addition of the MT flanking sequences. All of the mice with the elastase-rGH gene or albumin-TGFα transgenes expressed them in the appropriate organs, whereas a much smaller fraction expressed these genes when the MT flanking regions were not included. The MT flanking sequences did not improve expression from either the mouse protamine I or rGH promoter/enhancers; in fact, the data suggest that the MT flanking sequences were inhibitory.

EXAMPLE 14

Regulation of Transgene Containing MT 5'/3' LCR and Heterologous Cistron to External Factors Rat GH mRNA levels in several organs from eight of the MT 5'/3' elastase-rGH transgenic mice from Example 13 were determined. Four of these mice were exposed to Zn in their drinking water prior to assaying mRNA. We included Zn in these experiments to ascertain whether there are any functional metal regulatory elements in the MT flanking regions, because we have shown previously that the metal regulatory region from the MT promoter can function in conjunction with the elastase enhancer/promoter (Ornitz et al., Mol. Cell. Biol. (1987) 7: 3466–3472). The regulatory effect of Zn on the various constructs containing MT 5'/3' LCR and heterologous cistron (see Example 13) is summarized below.

| Construct | Normal organ | Ectopic organ | Freq. | Expression (mol/cell) | Percent of normal organ |
|---|---|---|---|---|---|
| MT 5'/3'-rEI-rGH(intronless) | Pancreas | Liver | 8/8 | 305 | 6.6% |
|  |  | Intestine | 2/2 | 6 | 0.8% |
| MT 5'-rEI-uPA | Pancreas | Testes | 3/3 | 92 | 0.6% |
| MT 5'/3'-rEI-myc-ER-hGH | Not tested |  |  |  |  |
| MT 5'/3'-mA-TGF-alpha | Liver | Pancreas | 2/4 | 70 | 6.4% |
|  |  | Intestine | 2/4 | 785 | 82% |
|  |  | Skin | 1/1 | 200 | 5.9% |
| MT 5'/3'-mPI-mP-hGH | Testes | Intestine | 2/5 | 55 | 7.4% |
| MT 5'/3'-rGH-hGH | Pituitary | Liver | 1/5 | 37 | 7.4% |
|  |  | Intestine | 1/5 | 5 | 5.5% |

Surprisingly, we measured significant amounts of rGH mRNA in the liver, averaging about 6.6% of that found in the pancreas, in all of these mice; however, rGH mRNA was not found in any other organ examined, including heart, intestine, testis, ovary, brain, and spleen. The hepatic expression of rGH undoubtedly accounts for the enhanced growth of some of these mice compared to controls. Zn treatment had no effect on rGH mRNA levels in either pancreas or liver. Several other constructs also showed signs of ectopic expression when flanked by the MT sequences. In summary, the MT flanking regions appear to enhance expression in conjunction with some, but not all, enhancer/promoters and they may promote ectopic expression in other organs, although the ectopic expression pattern is unpredictable.

EXAMPLE 15

The MT 5'/3' LCR Does Not Appear To Have Instrinsic Enhancer Ability

To ascertain whether the MT flanking regions have enhancer activity, they were combined with a hGH reporter gene with a minimal (83 bp) promoter which responds well to heterologous enhancers including those from MT-I, elastase I and protamine I genes (*Ornitz et al.*, 1987; *Hammer et al., Mol. Cell. Biol.* (1987) 7: 2956–2967). An hGH gene that extends from −83 relative to the transcription start site, and thus lacks GHF/Pit I binding sites was constructed. The tissue distribution of hGH expression in 5 transgenic mice made with this hGH gene alone was compared to that obtained with 5 mice that carry this hGH gene flanked by the MT LCR sequences. Human GH mRNA was assayed by solution hybridization with oligo hGH 149; the numbers in parentheses represent the average amount of hGH mRNA per cell in those mice that had detectable mRNA. These results are summarized below.

| Organ | Frequency of Expression (mRNA mol/cell) Transgene | |
|---|---|---|
| | −83 hGH | MT 5'/3'-83hGH |
| Liver | 0/5 | 4/5 (138 mol/cell) |
| Kidney | 0/5 | 0/5 |
| Pancreas | 0/5 | 0/5 |
| Heart | 0/5 | 0/5 |
| Intestine | 4/5 (28 mol/cell) | 1/5 (515 mol/cell |
| Lung | 0/5 | 0/5 |
| Testes | 0/3 | 0/4 |
| Ovary | 1/2 (152 mol/cell) | 1/1 (100 mol/cell) |
| Brain | 0/5 | 0/5 |
| Pituitary | 3/5 (825 mol/cell) | 0/5 |

In the transgenics without the MT flanking regions, a small amount of hGH mRNA was detected in intestine and ovary; none was detected in liver, kidney, pancreas, brain, testis, heart or lung. There was, however, substantial expression in pituitary from 3 of the transgenic mice. In contrast, 4 out of 5 of the mice with the MT flanking regions gave a low, but significant, level of expression in the liver, averaging about 140 molecules/cell, but no hGH mRNA was detected in other organs except for one intestine and one ovarian sample. In conclusion, the MT flanking regions alter the expression pattern of this test gene with its minimal promoter, repressing expression in pituitary and stimulating it in the liver, but they do not appear to act as general enhancers.

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. In the production of a polypeptide in a transgenic mouse, the improvement comprising
    (i) using a transgenic mouse comprising a cell having incorporated into its genome an expression system comprised of a cistron operably linked to a DNA flanking sequence of a mammalian metallothionein gene; wherein said DNA flanking sequence comprises one or more of the DNase I hypersensitive sites found within 50 kilobases of the mammalian metallothionein gene and wherein said DNA flanking sequence confers to said cistron tissue-independent, copy number-dependent, position-independent expression, said cistron comprising
        (a) a vertebrate gene promoter DNA sequence which can be regulated by an agonist, and
        (b) a structural gene located 3' to said promoter DNA sequence that is transcriptionally responsive to said promoter sequence, and
    (ii) Administering the agonist to said mouse, whereby expression of said cistron is induced, and the polypeptide is produced.

2. The method of claim 1, wherein said cistron comprises a metallothionein promoter and said agonist is a heavy metal ion, asteroid, an endotoxin, or a cytokine.

3. The method of claim 2, wherein said heavy metal ion is an ion of iron, cobalt, nickel, copper, silver, gold, zinc, cadmium, mercury or bismuth, and said endotoxin is a bacterial lipopolysaccharide.

4. The method of claim 1, wherein DNase I hypersensitive sites of said DNA flanking sequence is surrounded by as little as 50 bp and up to 20 kb of flanking sequence.

5. The method of claim 1, wherein said vertebrate gene promoter DNA sequence which can be regulated by an agonist is a metallothionein promoter.

6. The method of claim 1, wherein said promoter is selected from the group consisting of a metallothionein promoter, mouse albumin promoter, mouse protamine I promoter, rat elastase I promoter, and rat growth hormone promoter.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:1:

TCTTGCAGGC GCAGGAGCTG 20

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: linear ( i i ) MOLECULE TYPE: cDNA ( x i ) SEQUENCE DESCRIPTION: SEQ ID NO:2:

GAAAACGGGG GTTTAGTAAA CAGGG 25

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: linear ( i i ) MOLECULE TYPE: cDNA ( x i ) SEQUENCE DESCRIPTION: SEQ ID NO:3:

CATTCCGAGA TATCTGGTGA A        21

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

CACCACGACT TCAACGTCC        19

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:5:

CATTCCGAGA TCTGGTGAA        19

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:6:

GGCTGGTGGG CACTGGAGTG GCAACTT        27

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:7:

GCATTGGCAA ACAGACTGGA CAAGGGCAT        29

( 2 ) INFORMATION FOR SEQ ID NO:8:

( i ) SEQUENCE CHARACTERISTICS:
        ( A ) LENGTH: 26 base pairs
        ( B ) TYPE: nucleic acid (C) STRANDEDNESS: unknown
(D) TOPOLOGY: unknown (ii) MOLECULE TYPE: cDNA to mRNA (xi) SEQUENCE DESCRIPTION: SEQ ID NO:8:

GCGGGGGAAA AAGGCGCAGG CGACAG 26